United States Patent
Greve

(10) Patent No.: US 7,715,000 B2
(45) Date of Patent: May 11, 2010

(54) PARTICLE DETECTION SYSTEM, AND LITHOGRAPHIC APPARATUS PROVIDED WITH SUCH PARTICLE DETECTION SYSTEM

(75) Inventor: Peter Ferdinand Greve, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 11/505,498

(22) Filed: Aug. 17, 2006

(65) Prior Publication Data
US 2008/0043228 A1 Feb. 21, 2008

(51) Int. Cl.
G01N 21/47 (2006.01)
(52) U.S. Cl. .................................. 356/237.3
(58) Field of Classification Search .... 356/237.2–237.3
See application file for complete search history.

(56) References Cited
U.S. PATENT DOCUMENTS

| | | | | |
|---|---|---|---|---|
| 5,917,590 A | * | 6/1999 | Greve | 356/237.3 |
| 5,986,761 A | * | 11/1999 | Crawforth et al. | 356/600 |
| 6,072,581 A | * | 6/2000 | Stephenson et al. | 356/521 |
| 2004/0217175 A1 | * | 11/2004 | Bobba et al. | 235/462.39 |
| 2006/0055917 A1 | * | 3/2006 | Higashi et al. | 356/237.1 |

* cited by examiner

Primary Examiner—Tarifur Chowdhury
Assistant Examiner—Tara S Pajoohi
(74) Attorney, Agent, or Firm—Sterne, Kessler, Goldstein & Fox P.L.L.C

(57) ABSTRACT

A lithographic apparatus has an illumination system that conditions a beam of radiation. A patterning support supports a patterning device, which serves to impart the beam of radiation with a pattern in its cross-section. A substrate support holds a substrate. A projection system projects the patterned beam of radiation onto a target portion of the substrate. A particle detection system detects a particle on a surface of an object. The particle detection system has a radiation source, which generates an illumination beam of radiation. The illumination beam of radiation is directed along a first optical path to a detection area at the surface of the object. A radiation detector receives a detection beam of radiation from the detection area along a second optical path. The length of the first optical path is made substantially equal to the length of the second optical path.

20 Claims, 5 Drawing Sheets

PARTICLE DETECTION SYSTEM, AND LITHOGRAPHIC APPARATUS PROVIDED WITH SUCH PARTICLE DETECTION SYSTEM

BACKGROUND

1. Field of the Invention

The present invention relates to a particle detection system, and to a lithographic apparatus provided with such a particle detection system.

2. Description of the Related Art

A lithographic apparatus is a machine that applies a desired pattern onto a substrate, usually onto a target portion of the substrate. A lithographic apparatus can be used, for example, in the manufacture of integrated circuits (ICs). In such a case, a patterning device, which is alternatively referred to as a mask or a reticle, may be used to generate a circuit pattern to be formed on an individual layer of the IC. This pattern can be transferred onto a target portion (e.g. including part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Conventional lithographic apparatus include so-called steppers, in which each target portion is irradiated by exposing an entire pattern onto the target portion at once, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

The imaging of the pattern including small structures is very sensitive to dust and other contamination of the patterning device, possibly protected by a pellicle, and the substrate. Therefore, before imaging, the patterning device (and/or the pellicle protecting the small structures thereof) and substrate are tested for contamination, in particular for particles. If a particle is detected on the patterning device or on the substrate, the particle may be accepted (thereby accepting a fault area on the substrate), or it may be removed, or the patterning device or substrate may be rejected.

In conventional lithographic apparatus, a particle detection system directs a beam of radiation, in particular (but not necessarily) monochrome radiation, i.e. radiation having substantially one wavelength, on a surface of an object, for example, but not limited to, the patterning device or the substrate. The object and/or the beam move in order to scan the surface of the object. When the beam of radiation engages the surface of the object, the radiation is partially reflected according to physical laws of reflection (an exit angle is identical to an angle of incidence with respect to a fictitious line perpendicular to the surface (the normal)). Another part of the incident radiation may enter the object, such as the patterning device or substrate, and is refracted (according to Snell's law). In both cases, the beam is anisotropically redirected. When the beam of radiation engages a contaminating particle, the radiation is scattered, i.e. reflected isotropically.

A radiation detector is positioned with respect to the surface and the beam of radiation such that radiation reflected on the surface is not incident on the detector, but a part of the radiation scattered, i.e. being reflected in substantially every direction, by a particle or other contamination is incident on the detector. Thus, the detector receives radiation only when the beam of radiation is scattered by a particle or other contamination. The beam of radiation towards the surface (hereinafter: the illumination beam) and the beam of radiation received by the radiation detector (hereinafter: the detection beam) follow separate paths in the radiation detection device to prevent crosstalk between the two paths. This is necessary because the illumination beam intensity usually is many orders of magnitude higher than the detection beam intensity.

Because of the limited space available, a particle detection system according to the prior art has optics which are folded to fit the particle detection system into the available space. A rotating faceted polygon is used for scanning the surface of an object along a scan line, while the object moves parallel to the plane of the surface in a direction essentially at right angles to the scan line. In the path of the illumination beam, optical components like one or more mirrors and one or more lenses, such as a scan lens, are used to produce an almost telecentric illumination of the surface of the object. In the path of the detection beam, optical components like one or more mirrors and one or more lenses, such as a cylinder lens for focusing the detection beam on or near the polygon for reduction of beam size, and another cylinder lens near the detector for making the detection beam stigmatic, are used to produce light on a detector when a particle is present on the surface of the object in the illumination beam. The illumination beam and the detection beam may use the same facet of the polygon, though at different places. Accordingly, although the illumination beam produces a spot on the surface of the object moving along the scan line, the detection beam is static after reflection on the polygon facet. As a result, a small detector can be used for the detection of particles on the scan line. The detector detects an amount of light scattered by a particle, which amount is processed in calibrated detection circuitry to produce a signal indicating the presence of a particle or not, and to give an indication of the particle size. Since the detector just collects light, the performance of the particle detection system is independent of a spot size on the detector.

A part of the radiation incident on the surface of the object enters the object and is refracted, as above mentioned. Inside the object, the beam may be refracted and/or diffracted by the pattern and/or reflected one or more times. Depending on a number of parameters, such as the material, the size, the geometry, and the like, a part of the radiation that entered the object will leave the object again in the direction of the detector. In that case, the detector detects radiation not being scattered by a particle. As a result a detection circuit receiving a signal from the detector determines that a particle is present, although no particle is actually present. Such a detected, but not actually present particle will hereinafter be referred to as a ghost particle.

Due to the continuing increase in density of the patterns on the objects as used in the semiconductor component manufacturing industry, such as a reticle, the occurrence of ghost particles becomes more probable, and presents a new and growing problem. Thus, there is a need for a particle detection device that is able to discriminate accurately between physically present particles and ghost particles.

The optical components used in the particle detection system are to be cost effective, meaning that the desired function must be performed while at the same time accepting optical aberrations to a degree which does not impair the functionality of the system. These aberrations result in a certain detection spot size on the detector. Besides that, in combination with an asymmetry of the optical layout that is desirable for a compactness of the particle detection system, the aberrations cause the detection spot to move slightly over the detector in a scanning process. This detection spot movement adds to the spot size on the detector, i.e. the used area of the detector, and thus undesirably makes the particle detection system more sensitive to ghost particles (since the ghost discrimination is based on spatial filtering requiring a small spot size).

SUMMARY

It is desirable to provide a particle detection system having a reduced sensitivity to ghost particles.

According to an embodiment of the invention, there is provided a particle detection system configured to detect a particle on a surface of an object. The particle detection system includes a radiation source configured to generate an illumination beam of radiation, which is directed along a first optical path to a detection area at the surface of the object. The particle detection system further includes a radiation detector configured to receive a detection beam of radiation from the detection area along a second optical path. The length of the first optical path is substantially equal to the length of the second optical path.

According to a further embodiment of the invention, there is provided a lithographic apparatus, which includes an illumination system configured to condition a beam of radiation, and a patterning support configured to support a patterning device. The patterning device serves to impart the beam of radiation with a pattern in its cross-section. The lithographic apparatus further includes a substrate support configured to hold a substrate, a projection system configured to project the patterned beam of radiation onto a target portion of the substrate, and a particle detection system configured to detect a particle on a surface of an object. The particle detection system includes a radiation source configured to generate an illumination beam of radiation, which is directed along a first optical path to a detection area at the surface of the object. The particle detection system further includes a radiation detector configured to received a detection beam of radiation from the detection area along a second optical path. The length of the first optical path is substantially equal to the length of the second optical path.

When according to an embodiment of the present invention the length of the illumination path is essentially matched with the length of the detection path, the undesirable detection spot movement is essentially eliminated. The reason for this is that in case of matched illumination and detection path lengths, the effects of optical aberrations in the separate paths cancel each other to a high degree. More specifically, the locations and angles of the respective beams where they hit surfaces of lenses in their paths may be optically identical, making the interactions with the lenses the same. The result is that the beam deflection produced by a scan lens is substantially the same for the illumination beam and the detection beam. Near the polygon, the illumination beam and the detection beam may be parallel to each other. As a consequence, there is a precise compensation of deflection angles of the illumination beam and the detection beam as a function of polygon facet movement.

An elimination of detection spot movement allows for the use of a detector having a small detection area. A particle detection system using such a detector having a small detection area is less prone to detect ghost particles.

In order to match the length of the illumination path with the length of the detection path, in one class of embodiments, a path length difference may be compensated in an optical sense. In another class of embodiments, a path length difference may be compensated in a mechanical sense.

In an embodiment, there is provided a device manufacturing method including (a) conditioning a beam of radiation; (b) patterning the beam of radiation with a patterning device to form a patterned beam of radiation; (c) projecting the patterned beam of radiation onto a substrate; and (d) detecting a particle on a surface of an object, the detecting including (i) illuminating a detection area on the surface of the object with an illumination beam, the illumination beam directed to the detection area along a first optical path; and (ii) directing at least a portion of the illumination beam from the illuminated area along a second optical path to a detector to detect the particle, wherein a length of the first optical path is substantially the same as a length of the second optical path.

BRIEF DESCRIPTION OF THE DRAWINGS

Embodiments of the invention will now be described, by way of example only, with reference to the accompanying schematic drawings in which corresponding reference numerals indicate corresponding parts or parts having a similar function, and in which:

FIG. 8b shows a side view of the embodiment of the rotatable polygon of FIG. 8a;

DETAILED DESCRIPTION

Figure 1:
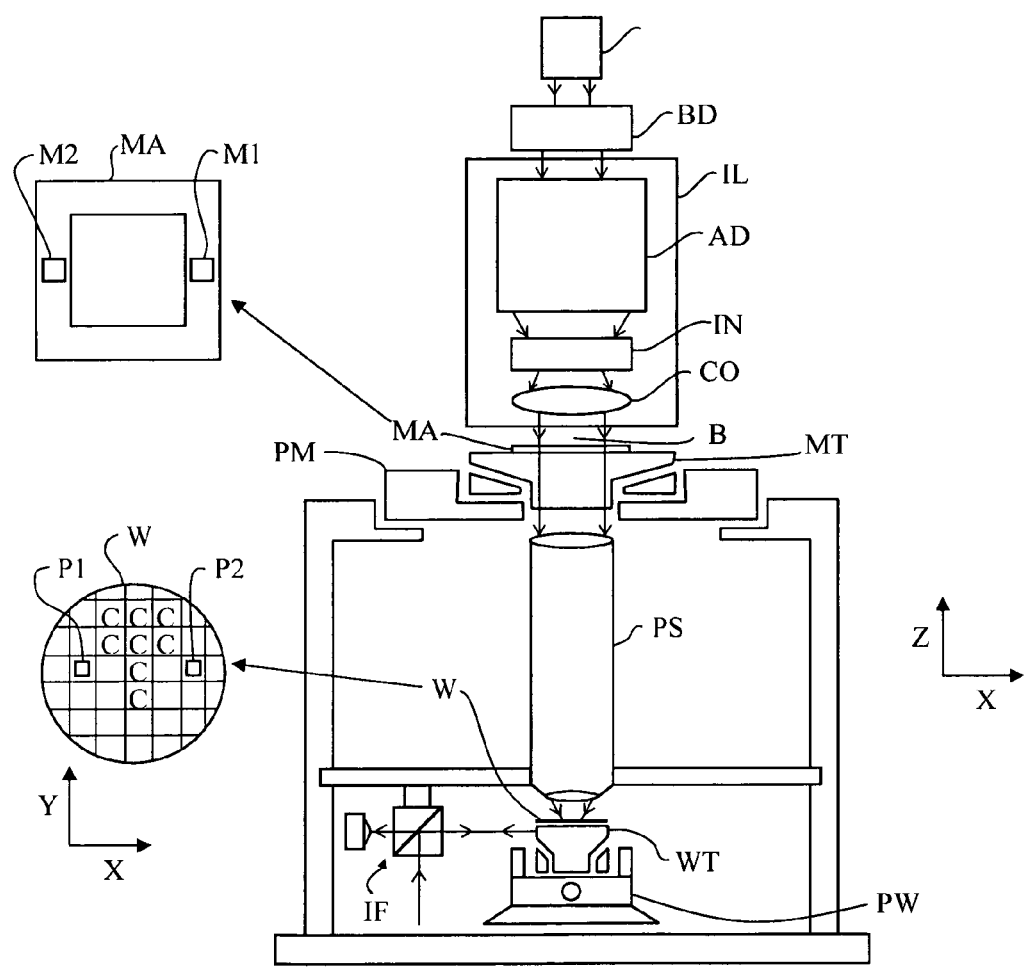
FIG. 1 depicts a lithographic apparatus according to an embodiment of the invention.

FIG. 1 schematically depicts a lithographic apparatus according to one embodiment of the invention. The apparatus includes an illumination system (illuminator) IL configured to condition a radiation beam B (e.g. UV radiation or any other suitable radiation), a mask support structure (e.g. a mask table) MT constructed to support a patterning device (e.g. a mask) MA and connected to a first positioning device PM configured to accurately position the patterning device in accordance with certain parameters. The apparatus also includes a substrate table (e.g. a wafer table) WT or "substrate support" constructed to hold a substrate (e.g. a resist-coated wafer) W and connected to a second positioning device PW configured to accurately position the substrate in accordance with certain parameters. The apparatus further includes a projection system (e.g. a refractive projection lens system) PS configured to project a pattern imparted to the radiation beam B by patterning device MA onto a target portion C (e.g. including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The mask support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The mask support structure can use mechanical, vacuum, electrostatic or other clamping techniques to hold the patterning device. The mask support structure may be a frame or a table, for example, which may be fixed or movable as required. The mask support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section so as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables or "substrate supports" (and/or two or more mask tables or "mask supports"). In such "multiple stage" machines the additional tables or supports may be used in parallel, or preparatory steps may be carried out on one or more tables or supports while one or more other tables or supports are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques can be used to increase the numerical aperture of projection systems. The term "immersion" as used herein does not mean that a structure, such as a substrate, must be submerged in liquid, but rather only means that a liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD configured to adjust the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the mask support structure (e.g., mask table MT), and is patterned by the patterning device. Having traversed the mask MA, the radiation beam B passes through the projection system PS, which focuses the beam onto a target portion C of the substrate W. With the aid of the second positioning device PW and position sensor IF (e.g. an interferometric device, linear encoder or capacitive sensor), the substrate table WT can be moved accurately, e.g. so as to position different target portions C in the path of the radiation beam B. Similarly, the first positioning device PM and another position sensor (which is not explicitly depicted in FIG. 1) can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioning device PM. Similarly, movement of the substrate table WT or "substrate support" may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT or "mask support" and the substrate table WT or "substrate support" are kept essentially stationary, while an entire pattern imparted to the radiation beam is projected onto a target portion C at once (i.e. a single static exposure). The substrate table WT or "substrate support" is then shifted in the X and/or Y direction so that a different target portion C can be exposed. In step mode, the maximum size of the exposure field limits the size of the target portion C imaged in a single static exposure.

2. In scan mode, the mask table MT or "mask support" and the substrate table WT or "substrate support" are scanned synchronously while a pattern imparted to the radiation beam is projected onto a target portion C (i.e. a single dynamic exposure). The velocity and direction of the substrate table WT or "substrate support" relative to the mask table MT or "mask support" may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT or "mask support" is kept essentially stationary holding a programmable patterning device, and the substrate table WT or "substrate support" is moved or scanned while a pattern imparted to the radiation beam is projected onto a target portion C. In this mode, generally a pulsed radiation source is employed and the programmable patterning device is updated as required after each movement of the substrate table WT or "substrate support" or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

To show the principle of particle detection by incident radiation and how artifacts may occur, it is illustrated in FIGS. 2-5 how isotropic, i.e. by a particle or other contamination scattered, and non-isotropic, e.g. diffracted or reflected, radiation may be incident on a detector system.

Figure 2:
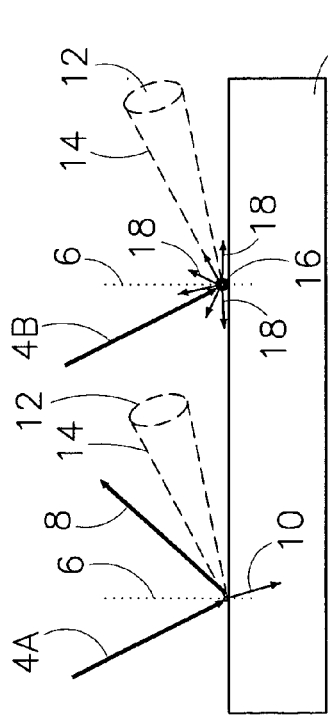
FIG. 2 schematically illustrates a redirection of a beam of radiation incident on an object or on a particle.

FIG. 2 shows an object 2 such as a lithographic mask or substrate, but not limited thereto. Referring to the left-hand side of FIG. 2, a beam 4A hits the surface of the object 2. At the location where the beam 4A hits the surface, the normal 6, i.e. a line perpendicular to the surface, is indicated. A reflection beam 8 may be reflected according to physical laws known to the person skilled in the art (an exit angle is the same as the angle of incidence with respect to the normal 6). The incident beam 4A may partially be refracted, indicated by a refraction beam 10. Depending on a refraction index of the material of object 2 and on the refraction index of the medium through which the radiation beam 4A travels, the refracted beam 10 is bent towards or away from the normal 6 (according to Snell's law). The amount of radiation being refracted and/or reflected depends on the material of object 2, a surface coating of the object 2 and/or on the angle of incidence, among others.

A schematically indicated detector system 12 detects radiation coming from the location of incidence of the radiation beam 4A, and being directed towards the detector system 12, indicated by a detection cone 14. As is seen from the left-hand side of FIG. 2, an incident beam 4A is anisotropically reflected as a reflection beam 8 and/or anisotropically refracted as a refraction beam 10. Thus, in this case, no radiation is incident on the detector and the detector may output a signal having a noise and/or bias level, but not having a significant particle detection level.

Now referring to the right-hand side of FIG. 2, a beam of radiation 4B is incident on a particle 16 present on the surface of object 2. A part of the incident radiation may be absorbed by the particle 16. Another part may be reflected. Due to the surface shape of the surface of the particle 16, the incident radiation is scattered, i.e. isotropically reflected. Isotropically reflected radiation, indicated by arrows 18 is directed in substantially every direction. Therefore, a part of the reflected radiation 18 lies within the detection cone 14 of the detector system 12. Thus, the detector system 12 detects radiation and outputs a signal corresponding to the detected radiation having a level above the particle detection level, i.e. a threshold level.

Figure 3:
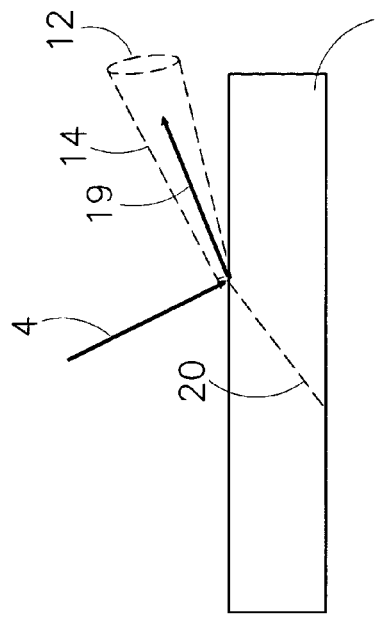
FIG. 3 schematically illustrates a beam of radiation leaving an object and being detected by a detector system.

In FIG. 3, an incident beam of radiation 4 is indicated to hit the surface of the object 2. From the location of incidence, a beam of radiation 19 lies within a detection cone 14 of detector system 12 and is incident on the detector system 12. The beam 19 may be radiation having been scattered by a contaminating particle, a detection circuit receiving a signal from the detector system 12 thus correctly detecting the particle.

However, a beam 20 coming from inside the object 2, as a result of diffraction, refraction and/or reflection as will be explained hereinafter, may leave the object 2 and be refracted such that the beam 19 results. So, if a beam 20 comes from inside the object 2 having such an angle with respect to the normal that its refracted beam 19 lies within the detection cone 14, the detector system 12 detects radiation which was not scattered by a contaminating particle. A detection circuit receiving a signal from the detector system 12 however determines that the signal is above a predetermined threshold level and erroneously indicates that a particle is present. Such a detected, but not actually present particle is herein referred to as a ghost particle.

As will be explained in detail below in relation to FIGS. 4 and 5, an important contributor to the detection of ghost particles is a diffraction pattern. When the object includes a pattern, for example a reflective chrome pattern at a surface, at which surface an entered radiation beam internally diffracts, a diffraction pattern may result. The diffraction pattern may internally reflect and refract and then exit the object such that at least a part of the diffraction pattern will be incident on the detector. Such a diffraction pattern is an anisotropic contribution to the radiation incident on the detector.

Figure 4:
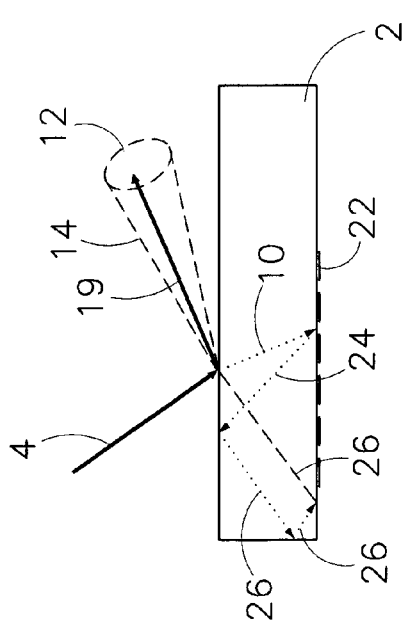
FIG. 4 schematically illustrates how a beam of radiation may be refracted, diffracted and/or reflected internally in an object before leaving the object in a direction of a particle detection system.

In FIG. 4, it is illustrated how a beam may originate from inside the object 2. The illustrated object 2 is a mask. On one surface, the mask 2 includes a mask pattern 22, which is made, for example, of chromium. An opposite surface of the mask 2 is scanned for particles. There is no particle actually present in the case illustrated in FIG. 4.

A beam 4 is directed at and incident on the surface to be scanned. A part of the incident radiation may be reflected (not shown) and another part may be absorbed and refracted. An absorbed and refracted beam 10 travels through the mask 2. At the opposite surface, the refracted beam 10 hits the mask pattern 22. The mask pattern 22 is a periodic pattern. Due to the periodicity the radiation is diffracted. A diffracted beam 24 travels through the mask 2 and is reflected at the surface of incidence. Subsequent internal reflections at other surfaces may occur, indicated by reflected beams 26. Eventually, an internally reflected beam 26 may approach the location of incidence of the beam 4 such that it leaves the mask 2 and is refracted towards the detector system 12 as indicated by the beam 19. Thus, a ghost particle is detected.

In FIG. 5, again, a refracted beam 19 coming from inside the mask 2 is incident on the detector system 12, but due to another series of reflections, refractions, and/or diffractions compared to the case illustrated in FIG. 4. In the case illustrated in FIG. 5, an incident beam 4 enters the mask 2 and is refracted as refracted beam 10. Given the angle of incidence and the surface conditions, the refracted beam 10 is diffracted or refracted at the opposite surface and leaves the mask 2 as diffracted beam 28. If the diffracted beam 28 is reflected at a surface 32 of another object, such as a pellicle, a reflected beam 26 may hit the surface of the mask 2 again.

The reflected beam 26 is diffracted by periodic mask pattern 22 and enters the mask 2 as a diffracted beam 30. The indicated diffracted beam 30 leaves the mask 2 such that it is refracted towards the detector system 12 and is detected. Similar to FIG. 4, a ghost particle is detected by a detection circuit, although no particle is present.

Figure 5:
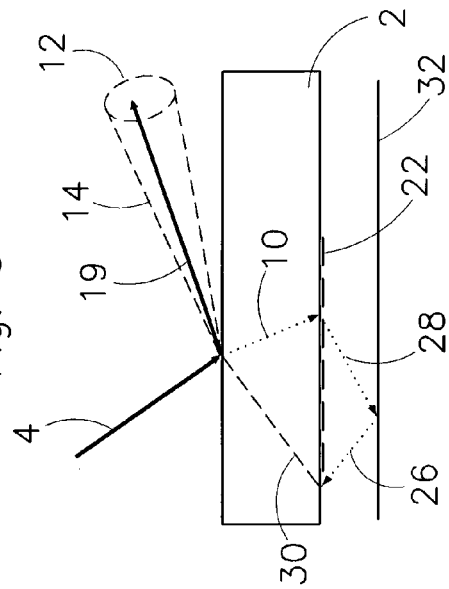
FIG. 5 schematically illustrates how a beam of radiation may be refracted, diffracted and/or reflected internally in an object or externally, before leaving the object in a direction of a particle detector.

In the above description in relation to FIGS. 3, 4 and 5, it should be noted that reflection, refraction and diffraction are anisotropic. The resulting redirected radiation is included in one or more beams as opposed to scattered, isotropic radiation being redirected in substantially every direction. The multiple diffracted beams are known as (diffraction) orders.

The cross-sections of the beams in a diffraction pattern are dependent on the shape of the cross-section of the incident beam of radiation. When, for instance, the incident beam is a single round beam of radiation, the diffraction pattern will be a series of single round beams. Finally, it is noted that FIGS. 2-5 are for illustrative purpose only, since many other light trajectories are possible.

Figure 6:
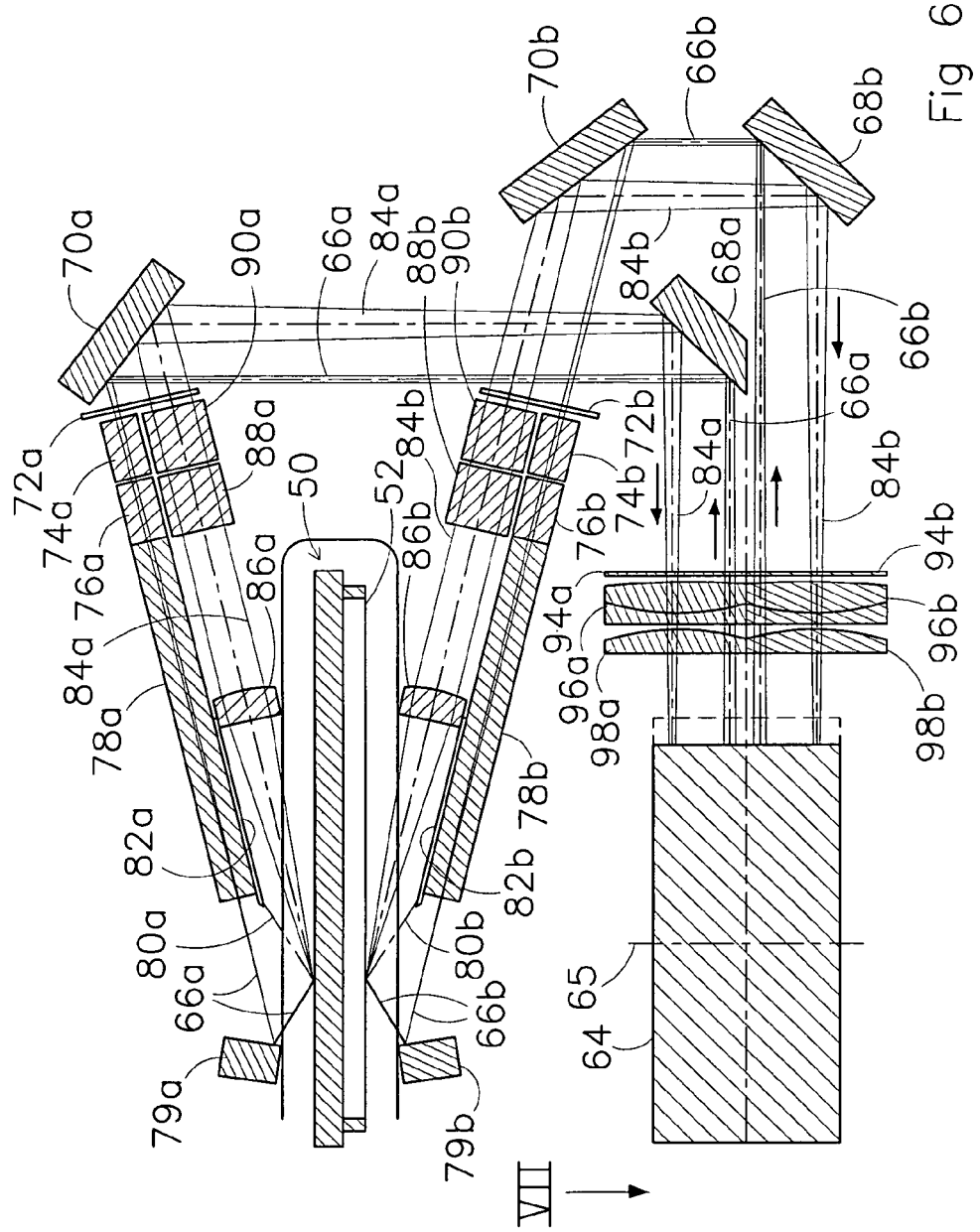
FIG. 6 shows a cross-sectional side view, according to arrow VI in FIG. 7, of a portion of a particle detection system according to an embodiment of the present invention.
Figure 7:
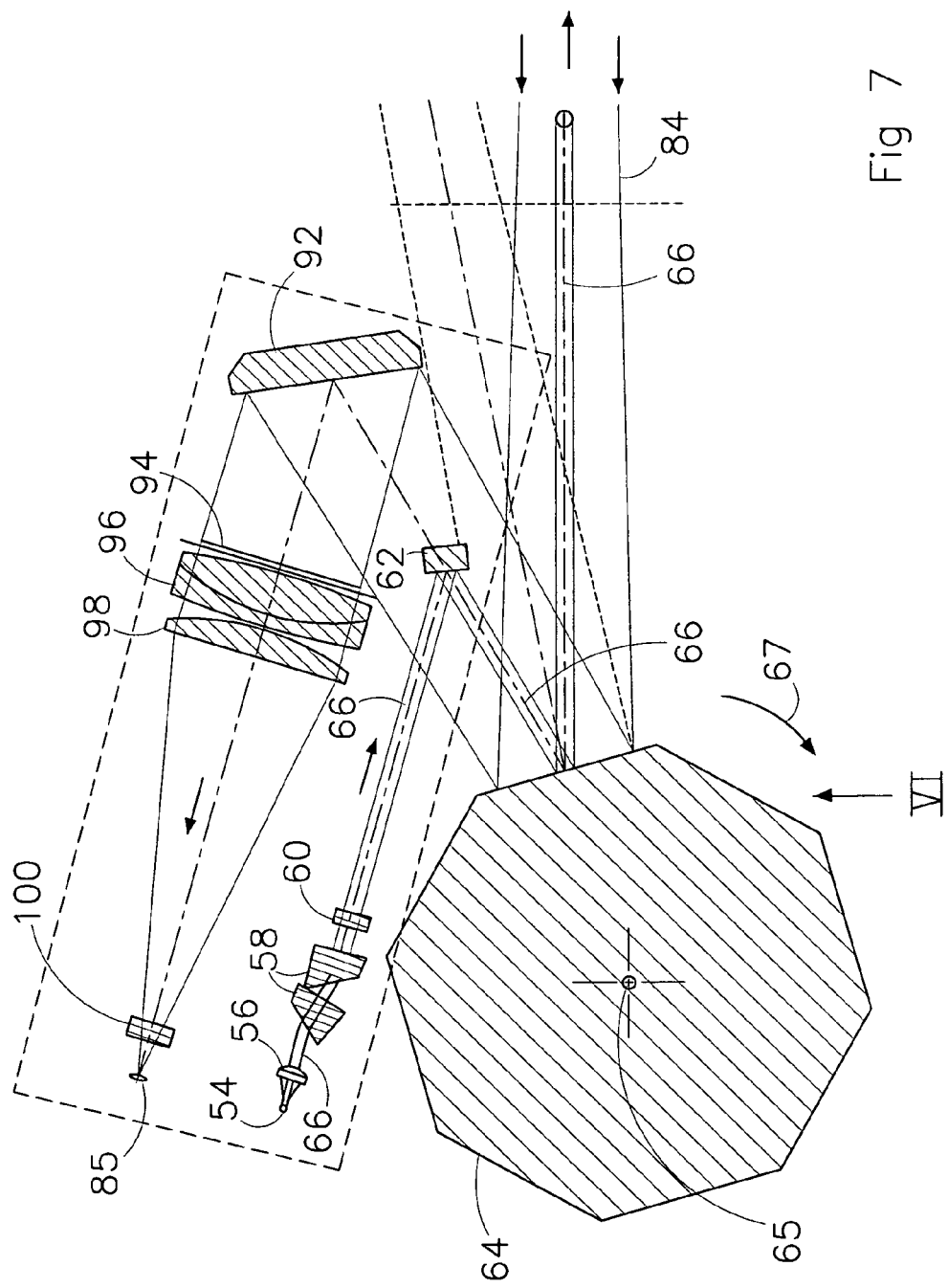
FIG. 7 shows a cross-sectional top view, according to arrow VII in FIG. 6, of a portion of a particle detection system according to an embodiment of the present invention.

FIGS. 6 and 7 show portions of a particle detection system according to an embodiment of the present invention for use in detecting particles on a surface of a patterning device 50. However, also the surface of other objects may be scanned. The embodiment shown includes in fact two functionally similar particle detection systems, a first particle detection system configured to detect particles on a top surface of the patterning device 50, and a second particle detection system configured to detect particles on a bottom surface of the patterning device 50, which bottom surface may be formed by a pellicle 52. In the following and in FIGS. 6 and 7, parts of the first particle detection system will be indicated by a reference numeral provided with a suffix a, and similar parts of the second particle detection system will be indicated by the same reference numeral provided with a suffix b. In FIG. 7 and other Figures, arrows having no reference numeral attached indicate a radiation beam direction.

A power laser 54 (FIG. 7) emits a beam of radiation (hereinafter: an illumination beam) 66 to a collimator lens 56. From the collimator lens 56, the illumination beam 66 passes through wedges 58 and a convergence lens 60, to be reflected by a first folding mirror 62, and then by a facet of a polygon 64 to be rotated about an axis 65, a direction of rotation being indicated by arrow 67, or in the opposite direction. The illumination beam 66a, 66b (FIG. 6) is reflected by a second folding mirror 68a, 68b and next by a third folding mirror 70a, 70b. Next, the illumination beam 66a, 66b passes a diaphragm 72a, 72b and scan lenses 74a, 74b and 76a, 76b supported by the diaphragm 72a, 72b. The illumination beam 66a, 66b then passes a compensation plate 78a, 78b and is next reflected on fourth folding mirror 79a, 79b to be directed to a top/bottom surface of the patterning device 50. The rotation of the polygon 64 causes the spot of incidence where the illumination beam impinges on the surface of the patterning device 50 to sweep over the surface from one side to an opposite side. If the surface at the area of the impinging illumination beam 66a, 66b does not have a particle thereon, and the top/bottom surface of the patterning device reflects the illumination beam, the reflected beam will follow a path 80a, 80b leading to a light trap plate 82a, 82b.

Any radiation scattered by a particle or generated in another way, and leading to a beam of radiation (hereinafter: a detection beam) 84a, 84b (FIG. 6) is led to a detector 85 through the following optical components in the path of the detection beam 84a, 84b. The detection beam 84a, 84b passes through a detection cylinder lens 86a, 86b and scan lenses 88a, 88b and 90a, 90b, passes an aperture in diaphragm 72a, 72b, to be reflected by the third folding mirror 70a, 70b and next by the second folding mirror 68a, 68b, and a facet of the polygon 64 consecutively. Next the detection beam 84 is reflected by a fifth folding mirror 92 (FIG. 7). After having been reflected by the fifth folding mirror 92, the detection beam 84 passes a detector stop 94, 94a, 94b, a detector doublet 96, 96a, 96b, a detector singlet 98, 98a, 98b, and a detector correction cylinder lens 100 to be directed to the detector 85. The detector 85 has a detection area where a detection beam 84 may form a detection spot.

It is to be noted that the number and nature of the optical components mentioned above, such as lenses and mirrors, in the path of the illumination beam 66a, 66b and in the path of the detection beam 84a, 84b may be varied, and merely have been shown and described by way of example. The scan lens pairs 74a, 76a and 74b, 76b may be optically identical to the scan lens pairs 88a, 90a and 88b, 90b.

As can be seen specifically in FIG. 6, an illumination beam and a detection beam of the first and second particle detection systems, respectively, are reflected on the same facet of the polygon 64, and spaced from each other vertically. On the facet of the polygon 64 in FIG. 6, from top to bottom, a detection beam 84a of the first particle detection system, an illumination beam 66a of the first particle system, an illumination beam 66b of the second particle detection system, and a detection beam 84b of the second particle detection system can be seen.

The compensation plate 78a, 78b functions to reduce the optical path length of the illumination beam 66a, 66b, thereby making the optical path length of the illumination beam 66a, 66b essentially equal or almost equal to the optical path length of the detection beam 84a, 84b. As a consequence, during scanning of the surface of an object, virtually no detection spot movement occurs on the detection area of the detector 85, allowing for a small dimension of the detection area, and thereby reducing any detection of ghost particles. The compensation plate 78a, 78b may be made from one, two or more parts, whereby cost savings may be achieved. The reduction of the optical path length of a beam passing a compensation plate is proportional to the length of the path in the plate and the index of refraction of the plate material, according to Snell's law. For usual glasses, the optical path length reduction is about 0.3 times the length of the path in the plate. Further, it is observed that the compensation plate may be integrated with other optical components, such as a scan lens.

Figure 8A:
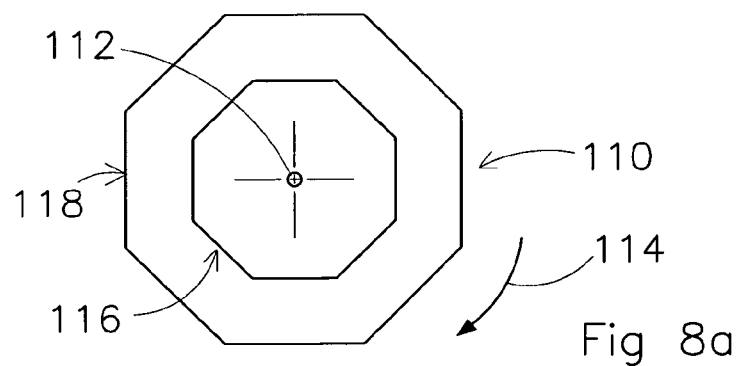
FIG. 8a shows a top view of an embodiment of a rotatable polygon to be used in an embodiment of a particle detection system according to the invention.
Figure 8B:
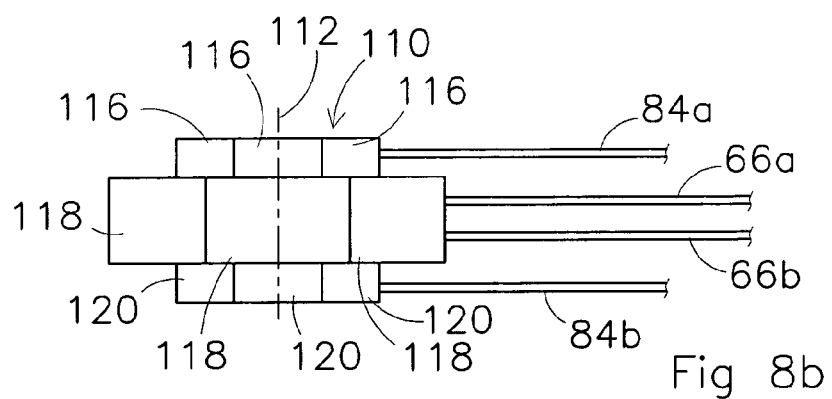

FIGS. 8a and 8b illustrate an embodiment of a polygon 110 configured to match the optical path length of the illumination beam 66a, 66b with the optical path length of the detection beam 84a, 84b in the absence of a compensation plate 78a, 78b. The polygon 110 is rotatable about an axis 112 in a direction indicated by arrow 114, or in the opposite direction. The polygon 110 includes a set of first facets 116 at a first axial position of the polygon 110, a set of second facets 118 of the polygon 110 at a second axial position of the polygon 110, and a set of third facets 120 of the polygon 110 at a third axial position of the polygon 110. The number of first facets 116 is equal to the number of second facets 118, and again equal to the number of third facets 120. A facet of the set of first facets 116 is parallel to a facet of the set of second facets 118, and again parallel to a facet of the set of third facets 120. A distance between a center of a first facet 116 and the axis 112 is different from a distance between a center of a second facet 118 and the axis 112, while a distance between a center of a third facet 120 and the axis 112 is the same as the distance between the center of the first facet 116 and the axis 112.

In use, an illumination beam 66a, 66b is reflected on the set of second facets 118 of the polygon 110, and a detection beam 84a, 84b is reflected on the set of first facets 116 and the set of third facets 120, respectively, whereby the optical path length of the illumination beam 66a, 66b is made substantially equal to the optical path length of the detection beam 84a, 84b.

Figure 9:
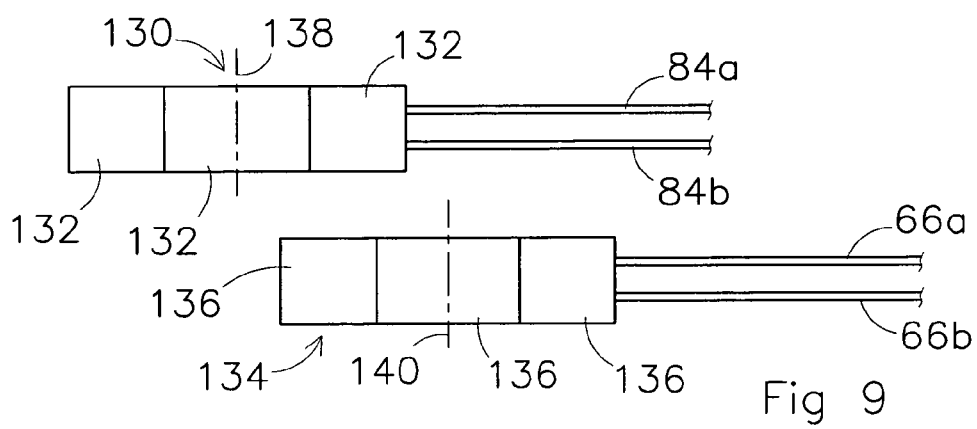
FIG. 9 shows a side view of an embodiment of an assembly of rotatable polygons to be used in an embodiment of a particle detection system according to the invention.

FIG. 9 shows a polygon assembly configured to match the optical path length of the illumination beam 66a, 66b with the optical path length of the detection beam 84a, 84b in the absence of a compensation plate 78a, 78b. The polygon assembly includes a first polygon 130 having a set of facets 132, and a second polygon 134 having a set of facets 136. The number of facets 132 is equal to the number of facets 136. The first polygon 130 and the second polygon 134 are rotatable about an axis 138 and 140, respectively in the same direction of rotation, while the rotation of the first polygon 130 is synchronized with the rotation of the second polygon 134. The axis 138 is parallel to and non-coaxial with the axis 140. In an alternative embodiment, however, the axis 138 may be coaxial with the axis 140. A distance between a center of a facet 132 and the axis 138 may be equal to, or different from a distance between a center of a facet 136 and the axis 140 in case of non-coaxial axes 138, 140. A distance between a center of a facet 132 and the axis 138 may be different from a distance between a center of a facet 136 and the axis 140 in case of coaxial axes 138, 140. A facet 132 of the first polygon 130 is parallel to a facet 136 of the second polygon 134.

In use, an illumination beam 66a, 66b is reflected on the set of facets 136 of the polygon 134, and a detection beam 84a, 84b is reflected on the set of facets 132 of the polygon 130, whereby the optical path length of the illumination beam 66a, 66b is made substantially equal to the optical path length of the detection beam 84a, 84b.

In the embodiments shown in FIGS. 6-9, polygons have sets of eight facets distributed evenly along the circumference of the polygon. It will be appreciated that sets with other numbers of facets may also be employed.

Figure 10:
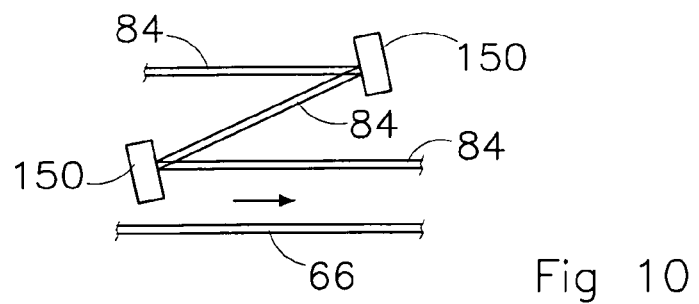
FIG. 10 shows a folding mirror arrangement to be used in an embodiment of a particle detection system according to the invention.

FIG. 10 shows an arrangement configured to match the optical path length of the illumination beam 66 with the optical path length of the detection beam 84 in the absence of a compensation plate 78a, 78b. FIG. 10 shows a part of the optical path of an illumination beam 66, and a part of the optical path of a detection beam 84. In the path of the detection beam 84, folding mirrors 150 are situated, thereby increasing the optical path length of the detection beam 84 to make the optical path length of the illumination beam 66 substantially equal to the optical path length of the detection beam 84.

It will be understood that instead of matching the optical path length of the illumination beam 66 with the optical path length of the detection beam 84 by increasing the optical path length of the detection beam 84 and/or decreasing the optical path length of the illumination beam 66 as illustrated in the above FIGS. 7-10, in other optical arrangements the optical path length of the detection beam 84 may be decreased and/or the optical path length of the illumination beam 66 may be increased if the situation so requires to match the optical path lengths of the illumination beam 66 and the detection beam 84 with each other. Measures according to embodiments of the present invention as described above and illustrated in FIGS. 6-10 may be employed in any combination.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention.

The terms "a" or "an", as used herein, are defined as one or more than one. The term plurality, as used herein, is defined as two or more than two. The term another, as used herein, is defined as at least a second or more. The terms including and/or having, as used herein, are defined as including (i.e., open language). The term coupled, as used herein, is defined as connected, although not necessarily directly, and not necessarily mechanically.

What is claimed is:

1. A particle detection system configured to avoid a false detection of a ghost particle on a surface of an object, the particle detection system comprising:
   a radiation source configured to generate an illumination beam of radiation, the illumination beam of radiation being directed along a first optical path to a surface of the object;
   a radiation detector configured to receive a detection beam of radiation reflected from the surface of the object along a second optical path; and
   a compensation plate configured and arranged to limit, by compensating a difference between the lengths of the first and the second optical paths, a movement of a detection spot where the detection beam is received on a detection area of the radiation detector such that the false detection of the ghost particle is avoided.

2. The particle detection system of claim 1, wherein at least one of the first optical path or the second optical path comprises the compensation plate so that a length of the first optical path is made substantially equal to a length of the second optical path, the compensation plate having a dimension in a first direction which is smaller than a dimension in a second direction at substantially a right angle to said first direction, wherein the at least one of the first optical path or the second optical path runs through the compensation plate in the direction of said second dimension.

3. The particle detection system of claim 1, wherein the first optical path comprises a set of first facets of a polygon that is rotatable about an axis, the second optical path comprising a set of second facets of the polygon, the number of first facets being equal to the number of second facets, a facet of the set of first facets being parallel to a facet of the set of second facets, and a distance between a center of the first facet and the axis being different from a distance between a center of the second facet and the axis.

4. The particle detection system of claim 1, wherein the first optical path comprises a set of first facets of a first polygon that is rotatable about a first axis, the second optical path comprising a set of second facets of a second polygon that is rotatable about a second axis, a number of first facets is equal to a number of second facets, and a facet of the set of first facets is parallel to a facet of the set of second facets, and the rotation of the first polygon being synchronized with the rotation of the second polygon so that a length of the first optical path is made substantially equal to a length of the second optical path.

5. The particle detection system of claim 4, wherein the first axis is substantially parallel to and non-coaxial with the second axis.

6. The particle detection system of claim 1, wherein at least one of the first optical path and the second optical path comprises a set of at least two mirrors configured to reflect the illumination beam of radiation and the detection beam of radiation, respectively.

7. The particle detection system of claim 1, wherein the first optical path is different from the second optical path.

8. The particle detection system of claim 7, wherein the first optical path is substantially parallel to the second optical path.

9. A lithographic apparatus comprising:
   an illumination system configured to condition a beam of radiation;
   a patterning support configured to support a patterning device, the patterning device serving to impart the beam of radiation with a pattern in its cross-section;
   a substrate support configured to hold a substrate;
   a projection system configured to project the patterned beam of radiation onto a target portion of the substrate; and
   a particle detection system configured to detect a particle on a surface of the patterning device, the particle detection system comprising:
      a radiation source configured to generate an illumination beam of radiation, the illumination beam of radiation being directed along a first optical path to a surface of the patterning device,
      a radiation detector configured to receive a detection beam of radiation reflected from the surface of the patterning device along a second optical path, and
      a compensation plate configured and arranged to limit, by compensating a difference between the lengths of the first and the second optical paths, a movement a detection spot on a detection area of the radiation detector such that a false detection of a ghost particle created from internal reflections of the detection beam inside the patterning device is avoided.

10. The lithographic apparatus of claim 9, wherein the first optical path is different from the second optical path.

11. The lithographic apparatus of claim 10, wherein the first optical path is substantially parallel to the second optical path.

12. The lithographic apparatus of claim 9, wherein at least one of the first optical path or the second optical path comprises the compensation plate so that a length of the first optical path is made substantially equal to a length of the second optical path, the compensation plate having a dimension in a first direction which is smaller than a dimension in a second direction at substantially right angle to said first direction, wherein the at least one of the first optical path or the second optical path runs through the at least one plate in the direction of said second dimension.

13. The lithographic apparatus of claim 9, wherein the first optical path comprises a set of first facets of a polygon that is rotatable about an axis and the second optical path comprises a set of second facets of the polygon, the number of first facets being equal to the number of second facets, a facet of the set of first facets being parallel to a facet of the set of second facets, and a distance between a center of the first facet and the axis being different from a distance between a center of the second facet and the axis.

14. The lithographic apparatus of claim 9, wherein the first optical path comprises a set of first facets of a first polygon that is rotatable about a first axis, the second optical path comprises a set of second facets of a second polygon that is rotatable about a second axis, the number of first facets is equal to the number of second facets, a facet of the set of first facets is parallel to a facet of the set of second facets, and the rotation of the first polygon is synchronized with the rotation of the second polygon.

15. The lithographic apparatus of claim 14, wherein the first axis is substantially parallel to and non-coaxial with the second axis.

16. The lithographic apparatus of claim 9, wherein at least one of the first optical path or the second optical path comprises a set of at least two minors configured to reflect the illumination beam of radiation and the detection beam of radiation, respectively, whereby a length of the first optical path is made substantially equal to a length of the second optical path.

17. A device manufacturing method comprising:
   (a) conditioning a beam of radiation;
   (b) patterning the beam of radiation to form a patterned beam of radiation;

(c) projecting the patterned beam of radiation onto a substrate; and
(d) detecting a particle on a surface of an object, the detecting comprising
  (i) illuminating a detection area on the surface of the object with an illumination beam, the illumination beam being directed to the detection area along a first optical path,
  (ii) directing at least a portion of the illumination beam from the illuminated area along a second optical path to a detector to detect the particle, and
  (iii) compensating to make the first optical path length substantially equal to the second optical path length, wherein the compensating comprises reducing a dimension of a detection area on the detector by reducing a movement of a detection spot on the detector such that a false detection of a ghost particle is avoided.

18. The method of claim 17, wherein the object is the patterning device.

19. The method of claim 17, wherein the first optical path is different from the second optical path.

20. The method of claim 19, wherein the first optical path is substantially parallel to the second optical path.

* * * * *